United States Patent [19]

Rowe et al.

[11] Patent Number: 5,208,249

[45] Date of Patent: May 4, 1993

[54] METHOD FOR STIMULATING INTRACELLULAR SYNTHESIS OF GLUTATHIONE USING ESTERS OF L-2-OXOTHIAZOLIDINE-4-CARBOXYLATE

[75] Inventors: W. Bruce Rowe, Evanston; Dennis I. Goldberg, Palatine, both of Ill.

[73] Assignee: Clintec Nutrition Co., Deerfield, Ill.

[21] Appl. No.: 932,761

[22] Filed: Aug. 20, 1992

[51] Int. Cl.$^5$ ............................................. A61K 31/425
[52] U.S. Cl. .................................................. 514/369
[58] Field of Search ......................................... 514/369

[56] References Cited

U.S. PATENT DOCUMENTS

| | | | |
|---|---|---|---|
| 4,335,210 | 6/1982 | Meister et al. | 435/113 |
| 4,434,158 | 2/1984 | Meister et al. | 424/94.63 |
| 4,438,124 | 3/1984 | Meister et al. | 514/369 |
| 4,647,571 | 3/1987 | Meister et al. | 514/369 |
| 4,665,082 | 5/1987 | Meister et al. | 514/365 |
| 4,710,489 | 12/1987 | Meister et al. | 514/18 |
| 4,784,685 | 11/1988 | Meister et al. | 71/106 |
| 5,095,027 | 3/1992 | Goldberg et al. | 514/369 |

FOREIGN PATENT DOCUMENTS 0373002  6/1990  European Pat. Off. .

Primary Examiner—Marianne M. Cintins
Assistant Examiner—Michael B. Hydorn
Attorney, Agent, or Firm—Hill, Steadman & Simpson

[57] ABSTRACT

A method for stimulating the intracellular synthesis of glutathione comprising the step of administering to a mammal a therapeutically effective amount of an ester of 2-oxothiazolidine-4-carboxylate is provided.

20 Claims, No Drawings

METHOD FOR STIMULATING INTRACELLULAR SYNTHESIS OF GLUTATHIONE USING ESTERS OF L-2-OXOTHIAZOLIDINE-4-CARBOXYLATE

BACKGROUND OF THE INVENTION

The present invention relates to methods for increasing cellular levels of glutathione and treatments utilizing same.

It is known that the intracellular levels of glutathione can be important with respect to cell function. For example, reduced glutathione levels are found in many disease states, e.g., immune compromised patients.

Further, it is known that glutathione provides many benefits in protecting cells against damage. For example, glutathione protects cells against the effects of free radicals and of oxygen intermediates. Free radicals are molecules with an unpaired electron creating an unstable and highly reactive molecule. Oxygen free radicals are highly reactive with biological macromolecules such as found in cell membranes and thereby can induce cell damage.

Indeed, a number of methods of treatments have been devised using the stimulation of intracellular glutathione levels to treat a number of disease states. Such disease states include: reperfusion injury (see U.S Pat. No. 5,095,027); hepatic disease; adult respiratory distress syndrome; immune disorders; and latent viral infections.

Unfortunately, according to the majority of literature in the art, intracellular glutathione levels cannot be increased by merely attempting to load the cell with glutathione. See, U.S. Pat. No. 4,784,685 "there are several reports on particular biological systems indicating that glutathione itself is not transported into cells" (column 2, lines 37-39).

Some methods are known to increase cellular levels of glutathione. Glutathione is composed of three amino acids: glutamic acid; cysteine; and glycine. Although administration to animals of the amino acid precursors of glutathione may produce an increase in cellular glutathione, there is a limit to the effectiveness of this procedure.

Concentrations of glutathione are dependent on the supply of cysteine. Cysteine can be derived from dietary protein and by trans-sulfuration from methionine in the liver. Cysteine administration is not an ideal method for increasing intracellular glutathione concentrations. Cysteine is rapidly metabolized and is very toxic (see U.S. Pat. No. 4,434,158 "cysteine cannot be administered intravenously due to its toxic effects on the system" (column 2, lines 6-8)).

A couple of compounds are known for increasing glutathione levels in the cells. For example, it is known to administer N-acetyl-L-cysteine, L-2-oxothiazolidine-4-carboxylate, and glutathione esters. Examples of patents relating to L-2-oxothiazolidine-4-carboxylate and glutathione esters are as follows: 4,335,210; 4,434,158; 4,438,124; 4,647,751; 4,665,082; 4,710,489; and 4,784,685.

L-2-oxothiazolidine-4-carboxylate is transported into most cells where it is converted by the action of 5-oxo-L-prolinase in the presence of adenosine triphosphate to produce S-carboxyl cysteine. S-carboxyl cysteine is then decarboxylated to produce cysteine. Cysteine is then rapidly used for glutathione synthesis.

There may be at least certain advantages achieved by L-2-oxothiazolidine-4-carboxylate over N-acetyl-L-cysteine and/or glutathione esters. These potential advantages the inventor believes include, inter alia, the fact that L-2-oxothiazolidine-4-carboxylate is more rapid and has better bioavailability as a precursor of cysteine; in certain circumstances, it is preferable to supply adequate cysteine to restore or maintain cellular functions including glutathione synthesis.

However, there are some cells and body tissues wherein it is difficult to transport L-2-oxothiazolidine-4-carboxylate into the cells. Such cells may include at least select brain cells, spinal cord cells, peripheral cells in the nervous system, skin, and the cornea. Some such cells may lack a mechanism for transporting L-2-oxothiazolidine-4-carboxylate into the cells. Even in cells having the ability to transport L-2-oxothiazolidine-4-carboxylate into the cells, the transport may be rate limiting as to the production of glutathione. Therefore, it may be desirable to bypass the transport. Still further, in some structures, such as the cornea or skin, cornified protective surfaces may prevent the transport of L-2-oxothiazolidine-4-carboxylate into the cells.

Although L-2-oxothiazolidine-4-carboxylate provides a mechanism for increasing intracellular glutathione levels in most cells, there are some cells and tissues wherein this mechanism cannot be used or one may want to avoid the mechanism.

SUMMARY OF THE INVENTION

The present invention provides a method for stimulating the intracellular synthesis of glutathione comprising the step of administering to a mammal a therapeutically effective amount of an ester of 2-oxothiazolidine-4-carboxylate. Preferably, the ester includes one to ten carbon atoms. In an embodiment, the ester is chosen from the group consisting of methyl, ethyl, propyl, isopropyl, butyl, isobutyl, and tertiary butyl esters.

Additionally, pursuant to the present invention, a method is provided for stimulating the intracellular synthesis of glutathione in cells not readily penetratable by L-2-oxothiazolidine-4-carboxylate comprising the step of administering to a patient a therapeutically effective amount of an ester of 2-oxothiazolidine-4-carboxylate in an amount sufficient to stimulate the intracellular synthesis of cells that are not readily penetratable by L-2-oxothiazolidine-4-carboxylate.

In an embodiment, the ester is administered to stimulate the intracellular synthesis of glutathione in cells chosen from the group consisting of the brain, skin, spinal cord, peripheral nervous system, or cornea cells of a patient.

Still further, the present invention provides a topical compound for stimulating intracellular glutathione synthesis. The compound comprises an active ingredient consisting of an oil of 2-oxothiazolidine-4-carboxylate that is a liquid at room temperature.

An advantage of the present invention is to provide a method for stimulating the intracellular synthesis of glutathione utilizing an ester of 2-oxothiazolidine-4-carboxylate.

A further advantage of the present invention is to provide a composition that can be used to stimulate the intracellular synthesis of glutathione in cells that are not readily penetratable by L-2-oxothiazolidine-4-carboxylate.

Additionally, an advantage of the present invention is to provide a composition that can be used to stimulate intracellular synthesis of glutathione in cells of tissues that include cornified protective surfaces.

Furthermore, an advantage of the present invention is to provide a method for creating esters of 2-oxothiazolidine-4-carboxylate.

Further, an advantage of the composition of the present invention is that it can supply adequate cysteine to restore or maintain cellular functions including glutathione synthesis.

Still further, an advantage of the present invention is that it provides a composition that is an oil at room temperature and therefore can be used advantageously in certain products, such as topical creams, ointments, and lotions.

Moreover, an advantage of the present invention is to provide a composition that can be used on tissues that are sensitive to irritants.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides a method for increasing the intracellular synthesis of glutathione. Pursuant to the method of the present invention, a therapeutically effective amount of an ester of 2-oxothiazolidine-4-carboxylate is administered to a patient. It has been found that the ester can be utilized to increase the intracellular synthesis of glutathione even in those cells that are not readily penetratable by L-2-oxothiazolidine-4-carboxylate.

In this regard, the inventor has found that the ester enhances lipophillicity of L-2-oxothiazolidine-4-carboxylate. Because the lipid solubility of L-2-oxothiazolidine-4-carboxylate is enhanced in the ester, the ester will penetrate cells into which L-2-oxothiazolidine-4-carboxylate is not readily transported. Such cells include, the inventor believes, at least certain of the cells of the brain, spinal cord, and peripheral nervous system tissue, as well as skin and cornea. By utilizing the composition of the present invention, a method can be provided for stimulating the intracellular synthesis of glutathione in these cells.

Additionally, due to the lipophillicity of the ester, the ester can be used for topical applications through a body's amphiphilic surfaces. Furthermore, the ester reduces the acidity of L-2-oxothiazolidine-4-carboxylate. Thus, in topical applications, the ester is specifically useful with respect to tissues that are at particular risk of irritability, for example, the tissues and organs of the eye.

The ester is a saturated straight or branched, alkyl group of 1 to 10 carbon atoms. Preferably, the ester is chosen from a saturated straight alkyl group such as methyl, ethyl, propyl, butyl, pentyl, hexyl, heptyl, octyl, nonyl, or decyl and a saturated branched alkyl group such as isopropyl, isobutyl, sec-butyl, tert-butyl, or isopenyl.

Although methyl, ethyl, propyl, isopropyl, butyl, and isobutyl are especially useful for medical applications, at this time, ethyl is most preferred. The ethyl ester appears to be the most biologically compatible.

Generally, the ester is prepared by reacting L-2-oxothiazolidine-4-carboxylate with an alcohol (ROH wherein R is an alkyl of 1 to 10 carbon atoms) in an acid catalyzed reaction, e.g., using hydrochloric, sulfuric, or phosphoric acid. The resulting compound can then be readily purified by crystallization. Preferably, ethanol is used to create the ethyl ester. However, other alcohols can be used as set forth above including methanol, propanol, isopropyl alcohol, butyl alcohol, isobutyl alcohol, and tertiary butyl alcohol. Of course, other methods can be used which lead to the pure ester.

The ester can be used to create compositions that can be administered enterally, parenterally, or topically.

An example of an enteral solution is as follows:

For enteral administration L-2-oxothiazolidine-4-carboxylate can be solubilized in any of the common triglyceride oils commonly used in enteral nutrition products such as soybean oil, canola oil, corn oil, or palm oil. For example, the L-2-oxothiazolidine-4-carboxylate ethyl ester is solubilized at a concentration of approximately 1 to about 8% in corn oil. The oil containing the active compound is then processed with other nutritional ingredients to form an emulsion that is compatible with oral intake and rapid gastrointestinal absorption.

An example of a parenteral solution is as follows:

For parenteral administration, L-2-oxothiazolidine-4-carboxylate ethyl ester can be prepared in a lipid emulsion that is compatible with intravenous administration. The L-2-oxothiazolidine-4-carboxylate ethyl ester is dissolved in a biologically compatible triglyceride such as soybean oil at a concentration of from approximately 1% (w/w) to about 10% (w/w). A sterile lipid emulsion is prepared by using a biologically compatible surfactant such as egg phospholipids and an agent such as glycerol to maintain osmotic balance when infused intravenously. The triglyceride component of the emulsion containing the active compound can be prepared from approximately 10% (w/w) to about 30% (w/w) of the emulsion to further vary the dosage of active agent.

For ophthalmic application of L-2-oxothiazolidine-4-carboxylate ethyl ester in a formulation designed for prolonged contact and slow release of the active agent, an ointment is prepared. The L-2-oxothiazolidine-4-carboxylate can be included in any non-irritant oil or lipid such as mineral oil or lanolin. In an embodiment, in the ophthalmic ointment, L-2-oxothiazolidine-4-carboxylate ethyl ester is solubilized at a concentration of approximately 2% (w/w) to about 4% (w/w) in a mixture of white petrolatum and anhydrous lanolin. This mixture is optimized for ease of applications and slow release of the active agent for overnight use. An appropriate amount of an oil soluble anti-microbial agent such as chlorobutanol is added to preserve sterility of the ointment.

An example of a topical ointment is as follows:

For topical applications of L-2-oxothiazolidine-4-carboxylate ethyl ester an ointment designed for rapid release of the active agent is prepared. This topical ointment is prepared to contain approximately 2% (w/w) to about 6% (w/w) of L-2-oxothiazolidine-4-carboxylate ethyl ester in a gelled mineral oil base. To prepare an ointment with convenient properties for application and retention on the skin, approximately 2 to about 5% (w/w) of low-density polyethylene is mixed with the oil containing the active agent and the mixture is heated and shock cooled to produce a colorless ointment with properties for convenient and effective applications on dermal surfaces with a broad range of surface and absorption characteristics.

By way of example, and not limitation, examples of the synthesis of the ester of the present invention will now be given:

EXAMPLE 1

Ten (10) grams of finely divided L-2-oxothiazolidine-4-carboxylic acid (OTC) were suspended in 150 ml of absolute ethanol without external cooling. A stream of dry hydrogen chloride gas was passed rapidly through this suspension until the OTC had gone into solution. The hot reaction mixture was then cooled in an ice bath while continuing the introduction of hydrogen chloride at a reduced rate to maintain saturation at 0°–5° C. After one hour, the reaction vessel was removed from the ice bath and closed with a calcium chloride drying tube to protect the reaction from atmospheric moisture.

After standing 3 to 4 hours at room temperature, a clear oil was formed in the reaction vessel. The reaction product was held overnight in the cold, then the supernatant was removed and the product was washed twice with cold absolute ethanol and twice with ether.

The resultant product was dried in vacuo over sodium hydroxide pellets. The product remained a clear oil at room temperature. However, if held in the cold, a quasi-crystalline mass was formed.

The quasi-crystalline material formed a clear slightly colored oil when returned to room temperature after standing in the cold for several days. Elemental analysis of the oil was consistent with that of the ethyl ester of L-2-oxothiazolidine-4-carboxylic acid.

EXAMPLE 2

A mixture of 50 grams of L-2-oxothiazolidine-4-carboxylic acid (OTC) and 63 grams (39 ml) of twice redistilled thionyl chloride was placed in a 1000 ml round bottom flask with 250 ml of n-propyl alcohol. The flask was fitted with a reflux condenser that was fitted with a calcium chloride guard tube. The flask was heated in a water bath for approximately one hour, until the evolution of HCl and sulfur dioxide ceased.

The reaction mixture was allowed to return to room temperature and 500 ml of ethyl ester was added. On standing in the cold overnight, a clear colorless oil was formed. The supernatant was poured off and the oil was washed twice with cold ethyl ether. The product was dried in vacuo over sodium chloride pellets.

After standing several days in the cold, a solid glass-like material formed which became a clear slightly colored oil at room temperature. Elemental analysis of the oil was consistent with that of the n-propyl ester of L-2-oxothiazolidine-4-carboxylic acid.

EXAMPLE 3

The esters of L-2-oxothiazolidine-4-carboxylate were also prepared by synthesis of esters of cysteine by refluxing the amino acid in HCl saturated solution of the parent alcohol such as methanol, ethanol, or n-propanol.

The ester hydrochloride of cysteine was then dissolved in an appropriate solvent and the L-2-oxothiazolidine-4-carboxylate ester was prepared as by the method of Kaneko et al, Bull. Chem. Soc. (Japan), Vol. 37, pp. 242–244 (1964) as modified by Shah et al, Cancer Research, Vol. 39, pp. 3942–3947 (1979).

By way of example, and not limitation, contemplative examples of methods of treatments pursuant to the present invention will now be given:

EXAMPLE 1A

A patient presented to the hospital emergency clinic with bilateral pain, swelling, lacrimation, and itching of the eyes. Keratitis of unknown etiology was diagnosed.

Since steroids are contraindicted in viral keratitis an ophthalmic ointment containing 2% L-2-oxothiazolidine-4-carboxylate ethyl ester was applied and a prescription was written with instructions to apply the ointment before retiring at night. An appointment was made with an ophthalmologist for 10 days later for a more complete diagnostic workup.

At the clinic visit, the patient reported that the pain, swelling, and itching was greatly diminished although excessive tearing still occurred. A diagnosis of herpes simplex keratitis was made and appropriate oral antiviral therapy was initiated.

EXAMPLE 2A

Conjunctivitis in one eye developed in a group of children ages 4–6 who attended a day camp together. Symptoms included foreign body sensation in the eye, lacrimation and swelling. On examination a focal erythema of the conjunctiva was noted.

An ophthalmic solution of 2% L-2-oxothiazolidine-4-carboxylate ethyl ester was prescribed for application every four hours and an ophthalmic ointment containing 2% L-2-oxothiazolidine-4-carboxylate ethyl ester was prescribed for application before retiring at night. When examined seven days later, the symptoms in all the children had diminished or disappeared and the ophthalmic ointment was continued until all symptoms had cleared. An adenoviral infection was suspected but not confirmed.

EXAMPLE 3A

At a preseason wrestling training camp in an unusually hot August in addition to the usual abrasions and rashes experienced by wrestlers, an outbreak of cutaneous herpes was noted. Eighteen of twenty-five athletes were noted to have erythematous vesicular lesions.

Because of concern for the consequences of steroid usage among athletes, the usual topical steroidal anti-inflammatory agents were not used. An ointment containing 5% L-2-oxothiazolidine-4-carboxylate ethyl ester was employed and a rapid clearing of the most serious lesions was noted. With increased vigilance for personal hygiene and mat cleaning, wrestling practice was continued with no further lesions noted. Anti-viral (acyclovir) was not required.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method for stimulating the intracellular synthesis of glutathione comprising the step of administering to a mammal a therapeutically effective amount of an ester of 2-oxothiazolidine-4-carboxylate for stimulating the intracellular synthesis of glutathione.

2. The method of claim 1 wherein the ester is chosen from the group consisting of alkyls having 1 to 10 carbon atoms.

3. The method of claim 1 wherein the ester of 2-oxothiazolidine-4-carboxylate is administered parenterally.

4. The method of claim 1 wherein the ester of 2-oxothiazolidine-4-carboxylate is administered enterally.

5. The method of claim 1 wherein the ester of 2-oxothiazolidine-4-carboxylate is administered topically.

6. The method of claim 1 wherein the ester is ethyl.

7. A method for stimulating the intracellular synthesis of glutathione in cells not readily penetratable by L-2-oxothiazolidine-4-carboxylate comprising the step of administering to a patient a therapeutically effective amount of an ester of 2-oxothiazolidine-4-carboxylate in an amount sufficient to stimulate the intracellular synthesis of cells that are not readily penetrated by 2-oxothiazolidine-4-carboxylate.

8. The method of claim 7 wherein the ester of 2-oxothiazolidine-4-carboxylate is administered to stimulate the intracellular synthesis of glutathione in the brain cells of a patient.

9. The method of claim 7 wherein the ester of 2-oxothiazolidine-4-carboxylate is administered to stimulate the intracellular synthesis of glutathione in at least select cells of the skin of a patient.

10. The method of claim 7 wherein the ester of 2-oxothiazolidine-4-carboxylate is administered to stimulate the intracellular synthesis of glutathione in cells located in the spinal cord of a patient.

11. The method of claim 7 wherein the ester of 2-oxothiazolidine-4-carboxylate is administered to stimulate the intracellular synthesis of glutathione in cells of the peripheral nervous system of a patient.

12. The method of claim 7 wherein the ester of 2-oxothiazolidine-4-carboxylate is administered to stimulate the intracellular synthesis of glutathione in cells of the cornea of a patient.

13. The method of claim 7 wherein the ester is selected from the group consisting of methyl, ethyl, propyl, isopropyl, butyl, isobutyl, and tertiary butyl esters.

14. The method of claim 7 wherein the ester of 2-oxothiazolidine-4-carboxylate is administered enterally.

15. The method of claim 7 wherein the ester of 2-oxothiazolidine-4-carboxylate is administered parenterally.

16. The method of claim 7 wherein the ester of 2-oxothiazolidine-4-carboxylate is administered topically.

17. A topical ointment capable of stimulating the intracellular synthesis of glutathione in at least cells to which the ointment is applied comprising:
 a therapeutically effective amount of an ester of 2-oxothiazolidine-4-carboxylate that is an oil at room temperature; and
 a mineral oil base.

18. The topical ointment of claim 17 wherein the ester is ethyl.

19. An ophthalmic ointment capable of stimulating the intracellular synthesis of glutathione in the cells of a patient's eye comprising:
 a therapeutically effective amount of an ester of 2-oxothiazolidine-4-carboxylate that is an oil at room temperature; and
 a base chosen from the group consisting of non-irritant oils and lipids.

20. The ophthalmic ointment of claim 19 wherein the base includes mineral oil.

* * * * *